United States Patent [19]

Lankinen

[11] Patent Number: 5,213,266
[45] Date of Patent: May 25, 1993

[54] INHALATION AEROSOL NOZZLE
[75] Inventor: Tapio Lankinen, Turku, Finland
[73] Assignee: Leiras Oy, Finland
[21] Appl. No.: 882,600
[22] Filed: May 13, 1992
[30] Foreign Application Priority Data
May 14, 1991 [FI] Finland .................. 912331
[51] Int. Cl.$^5$ .................. B05B 1/02; A61M 11/08
[52] U.S. Cl. ..............,................. 239/338; 239/573; 239/589; 128/200.23
[58] Field of Search ............. 239/338, 372, 573, 589, 239/598; 128/200.14, 200.23, 203.12

[56] References Cited
U.S. PATENT DOCUMENTS

| | | | |
|---|---|---|---|
| 2,818,202 | 12/1957 | Abplanalp | 239/573 X |
| 2,968,428 | 1/1961 | Samuel | 239/573 |
| 3,113,698 | 12/1963 | Abplanalp | 239/573 X |
| 3,302,834 | 2/1967 | Alsop | 239/338 X |
| 3,361,306 | 1/1968 | Grim | 128/200.23 X |
| 3,429,310 | 2/1969 | Jaffe et al. | 239/573 X |
| 4,145,005 | 3/1979 | Kirkel | 239/573 |
| 5,060,643 | 10/1991 | Rich et al. | 128/200.23 |
| 5,069,204 | 12/1991 | Smith et al. | 128/200.23 |

FOREIGN PATENT DOCUMENTS

| | | | |
|---|---|---|---|
| 219795 | 11/1958 | Australia | 239/338 |
| 660889 | 4/1963 | Canada | 128/200.23 |

Primary Examiner—Andres Kashnikow
Assistant Examiner—Wlllliam Grant
Attorney, Agent, or Firm—Browning, Bushman, Anderson & Brookhart

[57] ABSTRACT

The invention relates to an aerosol nozzle, comprising a socket (1) provided with an abutment surface for a hollow stem (2) in an aerosol container and therebelow an expansion chamber (3) with a nozzle orifice (4) in its wall. The distance between the bottom edge of nozzle orifice (4) and the abutment surface of socket (1) in the longitudinal direction of the socket does not exceed the outer radius of the hollow tube and that the nozzle orifice is located within a wall area defined by the end edge of the hollow tube and the intersecting line between such a cone and the wall of expansion chamber (3), which cone contacts the inner edge of the hollow stem, has its apex inside the hollow stem on its center line, and has a cone angle of 40°.

2 Claims, 5 Drawing Sheets

INHALATION AEROSOL NOZZLE

FIELD OF THE INVENTION

The present invention relates to an aerosol nozzle, comprising a socket provided with an abutment surface for the tapered stem of an aerosol container and therebelow an expansion chamber with a nozzle orifice in its wall.

BACKGROUND OF THE INVENTION

Inhalation aerosols are generally used for delivering medicament particles into the lungs, e.g. in the treatment of pulmonary asthma. It is necessary for successful medication that the particles be included in a sufficiently small size in inhalation air. However, it is generally known that only about 10% of a medicament dosage is capable of reaching its point of application in the lungs while most of it (about 80%) is retained in the upper respiratory tracts. The reasons for poor pulmonary penetration are known.

The inhalation aerosol consists of three main components: a medicament container, a metering valve mounted on the end thereof, and a plastic atomizer which contains a spray forming nozzle. During the course of dosage, a patient places the atomizer mouthpiece in his or her mouth, begins the oral inhalation and depressed the medicament container. Hence, the metering valve doses a certain volume of a propellant-medicament mixture which atomizes as a finely powdered spray into the mouth of a patient with some of the medicament finding its way into the lungs.

The only particles that can penetrate into the lungs in any significant degree are those whose diameter is 1-5 thousandths of a millimeter (microns). An inhalation aerosol spray only contains a small amount of such particles as most of the medicament is bound to considerably larger droplets formed by a non-volatile propellant; with one inhalation aerosol, the diameter of these droplets have been measured to be 43 microns at the moment of discharge.

The size of droplets is reduced as the volatilization of a propellant proceeds but, according to conducted studies, the volatilization of the largest droplets takes up to a couple of seconds. The non-volatile ingredients form a final particle, whose size is thus dependent on the size of a droplet issued from the nozzle as well as on the concentration of non-volatile ingredients therein.

When using an inhalation aerosol to measure a dose, the droplets arriving in the inhalation of a patient at a high speed mostly strike on the mucous membrane of the buccal cavity and a medicament contained therein does not reach the lungs. This portion of medicament is nearly inactive but, on the contrary, often leads to side effects. Also cold droplets may cause irritation. These negative effects can be mitigated by means of so-called inhalation chambers, wherein the medicament is sprayed prior to inhalation.

Studies have proved that nearly all inhalation aerosols produce particles too large for optimal pulmonary penetration. The problem is pronounced with medicaments having a relatively large single dose, the proportion of non-volatile ingredients being also large. Thus, it is obvious that by reducing the droplet size of a spray it is also possible to reduce the particle size and hence to improve the pulmonary penetration of a medicament. The volatilization or evaporation rate of small droplets is higher and their speed is reduced more rapidly as a result of air resistance. Such a spray is pleasant to a patient as the cold effect of a propellant is reduced.

Prior known factors having an effect on the droplet size include the pressure of a propellant and the diameter of a nozzle orifice (Polli, C.P., Grim, V.M., Bacher, F.A. and Yunker, M.H. (1969) J. Pharm. Sci. 58, 484–486) as well as the structure of a metering valve (Morch, F., (1978) Int. J. Pharm. 1, 213–218) and a nozzle (Pengilly, R.W. Keiner, J.A. J. Soc. Cosmet. Chem. (1977) 20:641–50). There is no published information dealing especially with the effect of the internal structure of a nozzle on the droplet and particle size of a spray.

SUMMARY OF THE INVENTION

A nozzle of the invention is characterized in that the distance between the bottom edge of a nozzle orifice and the abutment surface of a socket in the longitudinal direction of said socket does not exceed the outer radius of a hollow tube or stem and that the nozzle orifice is located within a wall area which is defined by the end edge of a hollow tube or stem and the intersecting line between such a cone and the wall of an expansion chamber, which cone contacts the inner edge of the hollow stem, has its apex inside the hollow stem on its center line, and has a cone angle of 40°.

When a conventional inhalation aerosol nozzle was applied to another purpose, it was necessary to locate the nozzle orifice right in the top section of an expansion chamber. It was unexpectedly discovered that such a nozzle produced a preferred very finely powdered spray. The development process involved manufacturing of 12 such nozzles, wherein the expansion chamber had a varying depth, shape and disposition of a nozzle orifice. The laboratory tests involved testing not only the droplet and particle size of sprays produced by the nozzles but also the effect thereon by the diameter of a nozzle orifice. It could be verified that, in an effort to produce a spray as finely powdered as possible, the most crucial factor was the location of a nozzle orifice. Nevertheless, the other above-mentioned factors, the depth, shape and nozzle orifice diameter of an expansion chamber, were also contributing factors but were more dependent on the dimensional volume of a metering valve employed.

The tests verified that a spray was all the more finely powdered the closer to the mouth of the hollow tube the nozzle orifice was located in the expansion chamber. It was also verified that the inner edge of a nozzle orifice had to be a sufficient distance out of the way of a mass flow issuing from the hollow tube in order to produce a spray as finely powdered as possible. This resulted in the above described structural limitations, whereby the structure or design will be distinctly different from prior known designs and a plastic atomizer containing the nozzle can be readily manufactured in a single piece, e.g. by injection molding.

BRIEF DESCRIPTION OF THE DRAWINGS

A device of the invention is illustrated in more detail in the accompanying drawings, in which.

DESCRIPTION OF THE PREFERRED EMBODIMENT

Figure 1A:
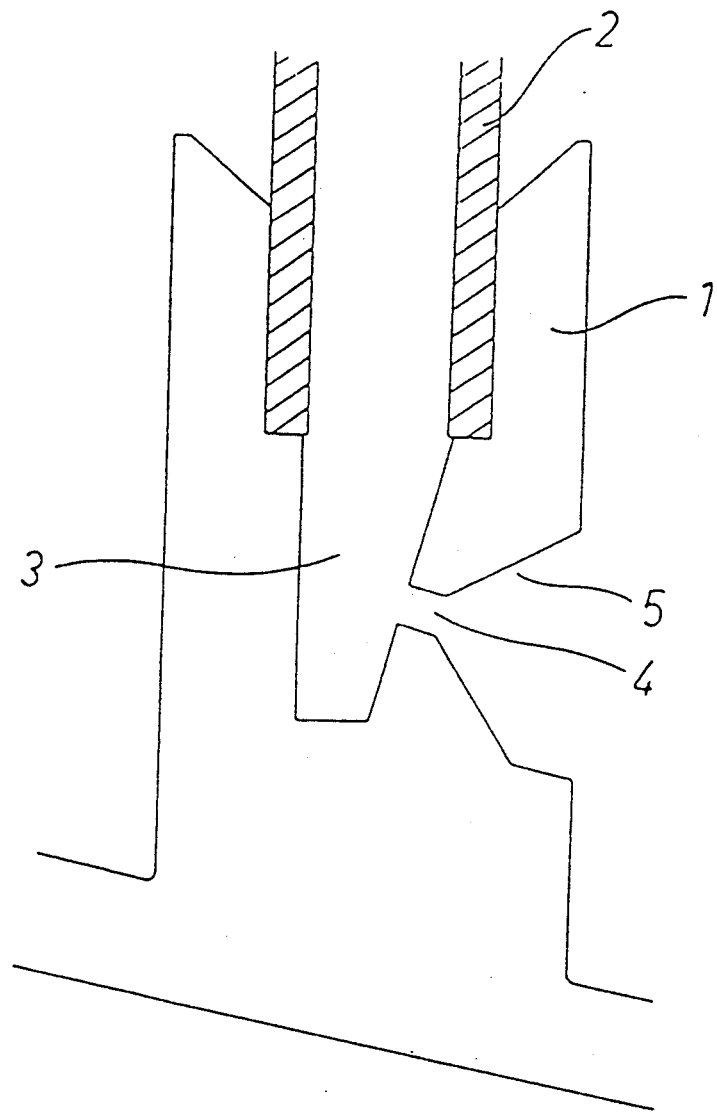
FIG. 1a shows a prior known nozzle with the nozzle orifice located in the bottom section of an expansion chamber.
Figure 1B:
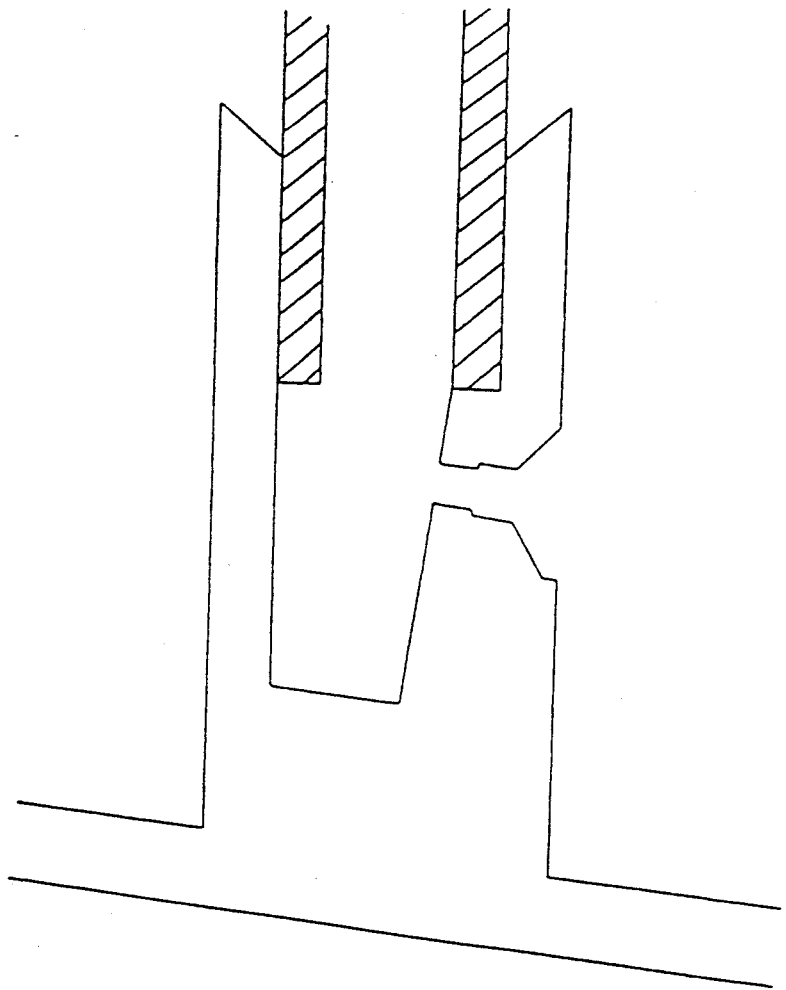
FIG. 1b shows a prior known nozzle with the nozzle orifice located in the top section of an expansion chamber.

A conventional nozzle design employed in inhalation aerosols is illustrated in FIGS. 1a and 1b. A hollow stem 2 fitting closely in a nozzle socket 1 comprises a circular tube, having a cross-section and an outer diameter of about 3 mm and through which a dose issuing from a metering valve finds its way into an expansion chamber 3. The wall of said expansion chamber is provided with a nozzle orifice 4, which is generally located in the middle or bottom section of a distance between the end of the hollow tube and the bottom of an expansion chamber (FIG. 1a), rarely in the top section thereof (FIG. 1b). The nozzle orifice generally opens into a conical or semi-spherical expansion 5 having a preferred spray atomizing effect. Such a nozzle assembly can be manufactured e.g. of plastics by injection molding in a single piece as part of a plastic atomizer. Prior known is also a design, wherein the nozzle orifice is fitted from outside with a separate spray-atomizing member for reducing the droplet size. Such a design is more expensive to manufacture, jams easily and is not widely used.

Figure 2:
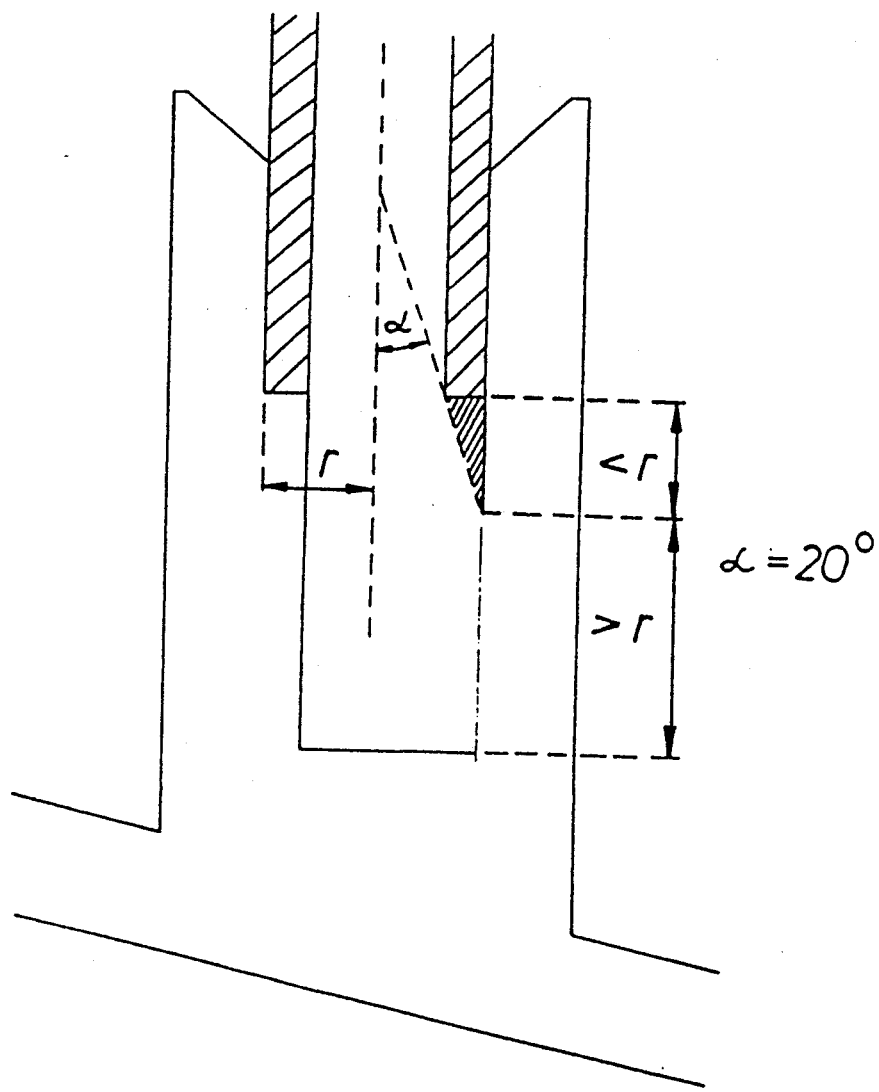
FIG. 2 illustrates the basic principle of the invention and FIGS. 3 and 4 show various embodiments of the invention.
Figure 3:
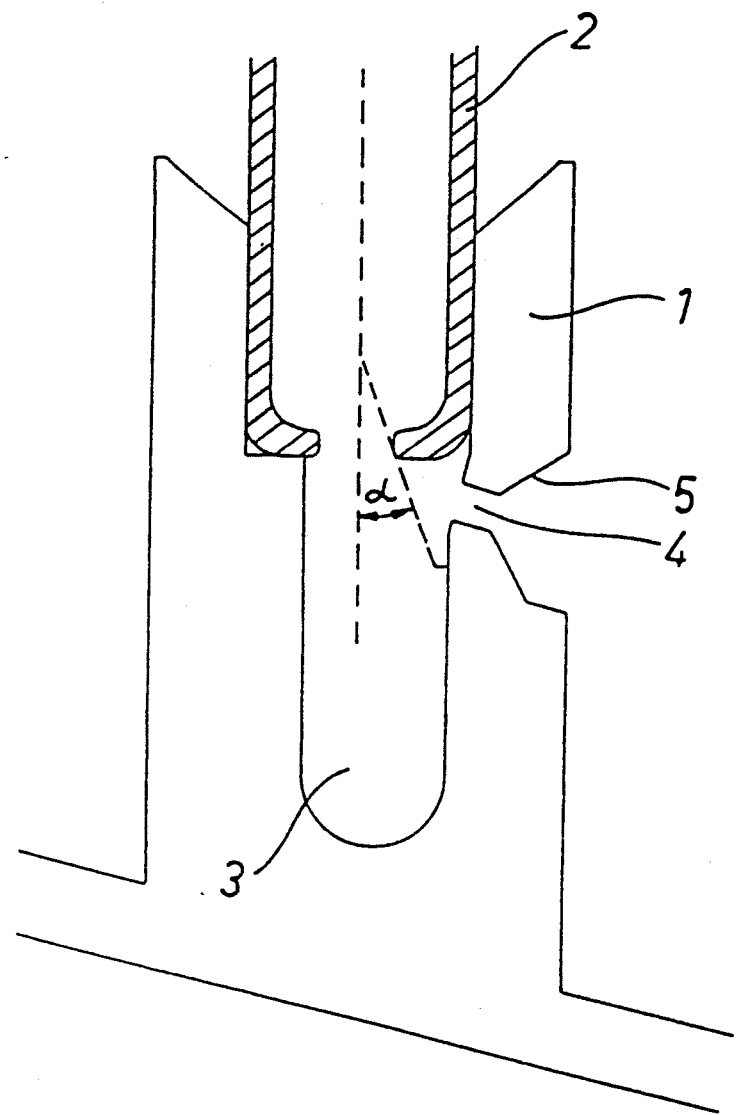
Figure 4:
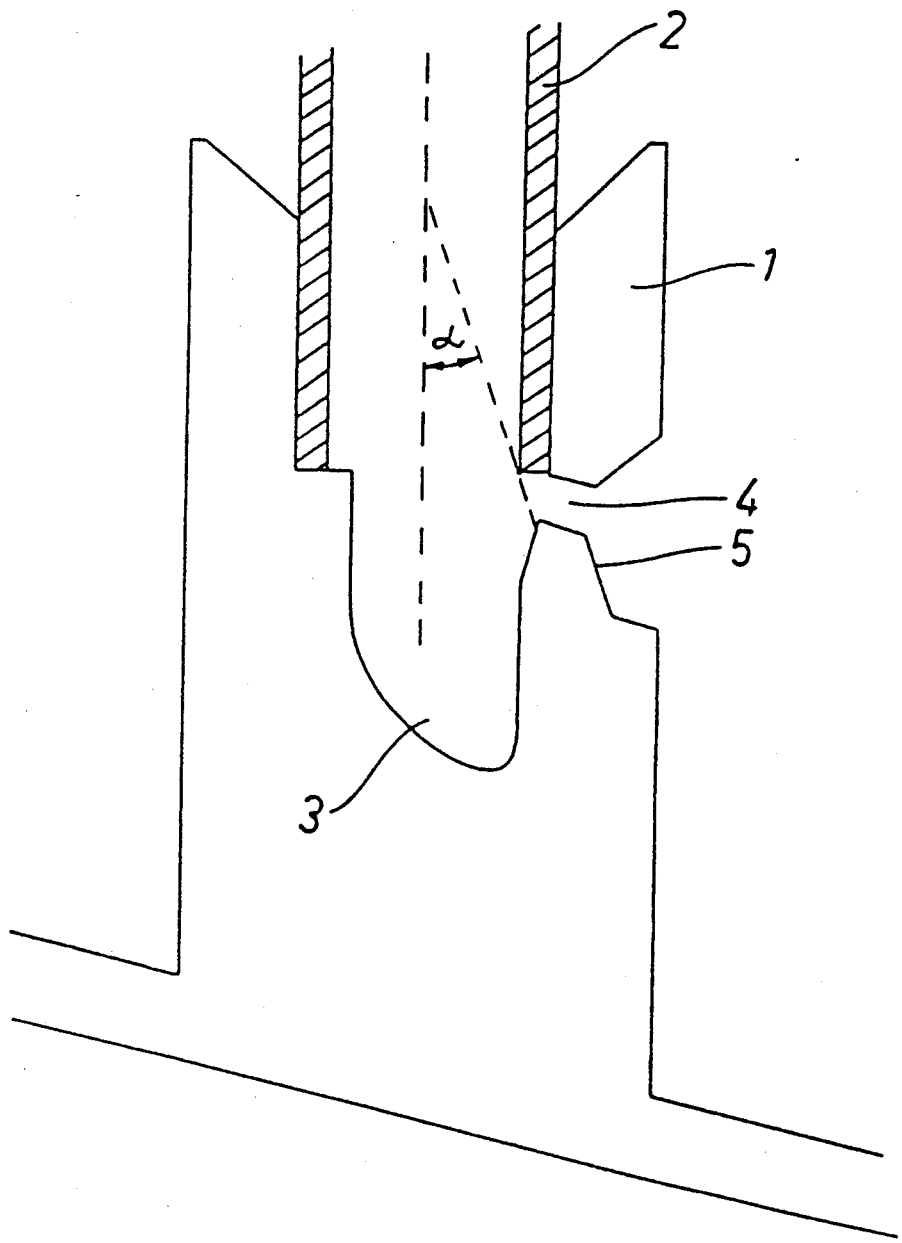

FIG. 2 shows a more detailed view of a nozzle assembly of the invention with its limiting dimensions. The expansion chamber 3 must be designed in a manner that a nozzle orifice 4 will be located within the shaded area. FIGS. 3 and 4 illustrate embodiments of the invention having different designs for hollow valve stems 2.

Thus, it should be noted that, in a nozzle of the invention, the location of nozzle orifice 4 also depends on the dimensioning of hollow valve stem 2 employed. In both embodiments, said nozzle 4 opens out as a conical expansion 5.

The efficiency of a nozzle of the invention was measured by two different methods: by measuring calorimetrically the proportion of a non-volatile propellant in a spray at the distance of 6 cm from nozzle orifice 4 as well as by measuring the particle distribution of a spray by means of a cascade impactor. According to the calorimetrical tests, a nozzle of the invention reduced the relative amount of a non-volatile propellant to less than half of the amount found in a conventional device. This means that the nozzle discharge smaller droplets from which the propellant evaporated at about doubled rate in test conditions.

The test carried out with a cascade impactor involved comparisons between aerosols from several different manufacturers fitted both with original nozzles and those of the invention. In every case, the latter was found to produce smaller particles. In the example cases, the mean particle size was reduced from 5.6 microns to 4.7 microns ("Lomudal" 1 mg/dose) and from 2.5 microns to 2.1 microns ("Ventoline" 0.1 mg/dose). In the former case, the volume of particles was thus reduced by appr. 40% and in the latter case by appr. 35%.

What is claimed is:

1. An aerosol nozzle comprising a socket (1) provided with an abutment surface for a hollow stem (2) in an aerosol container and therebelow an expansion chamber (3) with a nozzle orifice (4) in its wall, said nozzle orifice having a bottom edge, characterized in that said hollow stem has an end surface and an inner end edge, the distance between the bottom edge of said nozzle orifice (4) and the abutment surface of the socket (1) in the longitudinal direction of said socket does not exceed the outer radius of said hollow stem and that the nozzle orifice (4) is located within a wall area which is defined by the end surface of the hollow stem and a line extending from the centerline of said hollow stem and intersecting the inner end edge of said hollow stem and the wall of the expansion chamber (3), rotation of said line about said centerline defining a cone having its apex inside the hollow stem, said cone having an angle of 40°.

2. A nozzle as set forth in claim 1, characterized by being manufactured in a single piece.

* * * * *